United States Patent [19]

Agren

[11] Patent Number: 4,555,628
[45] Date of Patent: Nov. 26, 1985

[54] METHOD FOR MEASURING THE CAMOUFLAGING CAPACITY OF A SMOKE

[76] Inventor: Bengt-Ake Agren, Trumpetvägen 100, S-633 47 Eskilstuna, Sweden

[21] Appl. No.: 478,987

[22] Filed: Mar. 25, 1983

[30] Foreign Application Priority Data

Mar. 30, 1982 [SE] Sweden ............................... 8202007

[51] Int. Cl.$^4$ ............................................... G01S 5/16
[52] U.S. Cl. ..................................................... 250/341
[58] Field of Search .............. 250/341, 343, 342, 348, 250/338, 340, 575, 573; 256/438, 439

[56] References Cited

U.S. PATENT DOCUMENTS

| 3,478,211 | 11/1969 | Moser | 250/340 |
| 3,975,292 | 8/1976 | Shaffer | 250/342 |
| 3,985,452 | 10/1976 | Bylander et al. | 250/575 |
| 4,200,398 | 4/1980 | Persson et al. | 250/573 |

Primary Examiner—Alfred E. Smith
Assistant Examiner—Richard E. Hanig
Attorney, Agent, or Firm—Fleit, Jacobson, Cohn & Price

[57] ABSTRACT

Method for measuring the camouflaging capacity of a smoke. A selected radiation source, such as an IR radiation source, is divided into a predetermined number of IR radiating elements having mutually differing radiation temperatures. After the release of smoke between the radiating elements and an IR camera, the number of temperature peaks which cannot be distinguished with respect to the background temperature is employed as a measure of the IR camouflaging capacity of the smoke. When measuring the camouflaging capacity of the smoke over a wide area several groups of such IR-radiating elements are distributed over the area.

5 Claims, 6 Drawing Figures

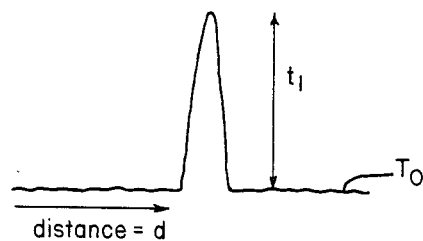 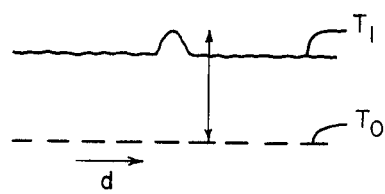
FIG. 1a  FIG. 1b
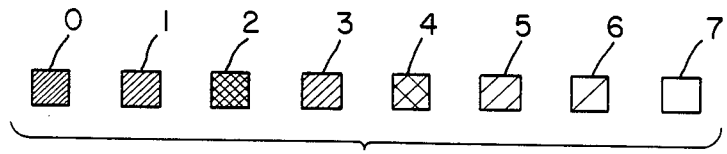
FIG. 2
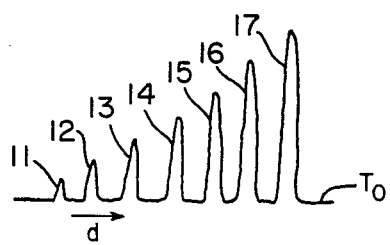 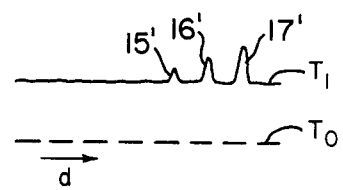
FIG. 3a  FIG. 3b
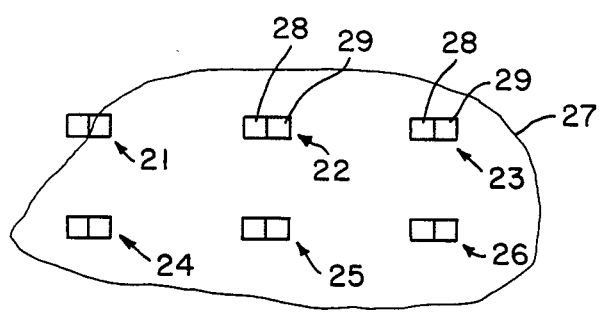
FIG. 4

METHOD FOR MEASURING THE CAMOUFLAGING CAPACITY OF A SMOKE

BACKGROUND

The present invention relates to a method for measuring the camouflaging capacity of a smoke, especially within the infra-red (IR) range, but also within the ultraviolet, the visual and the mm wave range.

During target seeking, especially for military purposes, use is often made of a target seeking camera, i.e. a camera which detects the radiation emitted from any object. One method for protecting such objects from being detected by such target seekers is hence to surround the object by a smoke which to a greater or lesser extent attenuates or absorbs the radiation from the object.

During the development of suitable smokes it has hitherto proved difficult to measure reliably the capacity of the smoke produced for camouflaging radiation. The conventional method for measurement is as follows regarding IR smoke.

After a suitable, known IR radiation source has been selected, an IR camera is aimed against the radiation source before the smoke is released. Measurements are then made of the radiation temperature $t_1$ of the radiation received from the IR radiation source. With the IR camera still directed against the IR radiation source, IR smoke is then released between the radiation source and the IR camera. Measurements are now made of lower radiation temperature $t_2$ on the part of the radiation from the IR radiation source. The difference $t_1 - t_2$ corresponds to the attenuation of the radiation received from the radiation source.

However the difference $t_1 - t_2$ provides no information as regards the degree to which the radiation source can, after smoke has been released, be differentiated with respect to the surroundings of the radiation source, because it provides no information as to the radiation temperature on the part of the surroundings. Hence the method does not provide any unequivocal measure of the camouflage capacity of the smoke.

The known method is particularly unsuitable when it is a question of comparing different types of smoke. A pyrotechnic aerosol, which is hot, and which thus itself emits IR radiation, gives a high background temperature which means that it becomes difficult to distinguish the radiation source, so that the smoke is deemed to have good camouflage capacity. A measurement of the said difference $t_1 - t_2$ can on the other hand indicate that the smoke gives low attenuation and hence that it would have poor camouflage capacity.

Corresponding disadvantage is present when measuring camouflaging smoke within the ultraviolet, the visual and the mm wave range.

Consequently the aim of the present invention is to provide a method of measuring the camouflaging capacity of smoke by means of which consideration is given on the one hand to the intensity of the background radiation and secondly a comparison can be made between the camouflaging capacity of hot (i.e. intensive radiating) or cold (i.e. weak radiating) smoke. This aim is achieved in that the method in accordance with the present invention is given the characteristics specified in claim 1. Further developments of the invention are described in the subclaims.

BRIEF DESCRIPTION OF THE DRAWINGS

The invention will be described in greater detail in the following by reference to the appended drawings which illustrate the method in accordance with the invention in schematic form in connection with measurement of the camouflaging capacity of a smoke within the infrared range.

FIGS. 1a and 1b illustrate a conventional method of measuring the IR attenuating capacity of a smoke. FIG. 2 Shows schematically the IR-radiating element employed with the procedure in accordance with the invention. FIGS. 3a and 3b show how the procedure in accordance with the invention is carried out. FIG. 4 illustrates a further embodiment of the invention.

DETAILED DESCRIPTION

As mentioned previously, the conventional method of measuring the IR attenuating capacity of an aerosol is that an IR camera is directed towards a selected radiation source, where the radiation temperature $t_1$ (see FIG. 1a) is detected by the IR camera. Then the smoke concerned is released between the radiation source and the IR camera, which now receives from the radiation source IR radiation at a temperature $t_2$ (see FIG. 1b). Here the difference $t_1 - t_2$ is employed as a measure of the quality of the smoke. Here no consideration is given to the fact that the background temperature level $T_0$, prevailing in the absence of smoke, has been increased to $T_1$ as a result of the discharge of smoke.

In accordance with the present invention a selected radiation source is now divided into n sections of IR radiating elements, where $n \geq 2$. In the embodiment illustrated in FIG. 2 the radiation source consists of eight sections of IR radiating elements in the form of black-body radiators 0-7, where the black-body radiator 0 comprises a background reference element having the same temperature as the background of the radiation source. The radiation temperature of elements 1-7 has been chosen to have values which increase consecutively, either in accordance with a linear or non-linear (e.g. exponential) increasing scale.

When an IR detector, e.g. an IR camera (not shown) is directed towards the black-body radiators 0-7, seven radiation temperature peaks 11-17 are detected from elements 1-7. No radiation peak is detected from element 0, because this element has the same temperature as the background. When subsequently the smoke concerned is discharged between elements 1-7 and the camera, the radiation received from elements 1-7 is attenuated.

At the same time however the background temperature level is increased from the value $T_0$ to $T_1$, dependent on the temperature of the smoke. As a result only a certain number of temperature peaks are distinguishable above the level $T_1$. In the example illustrated in FIG. 3b only the three peaks 15'-17' are distinguishable, although attenuated. On the other hand the other four peaks 11-14 cannot be distinguished because of the fact that the background temperature has increased. In accordance with the present invention it is now possible to employ the number of non-distinguishable radiation peaks (in the example shown, four) as a measure of the quality of the smoke. In the example shown the smoke can thus be given a quality figure between 0 and 7, comprising a measure of the camouflaging capacity of the smoke.

When measuring the camouflaging capacity of the smoke over a wide area it is possible to distribute in the desired manner several groups of the said IR radiating elements across the area. Each such group then contains at least two IR radiating elements. Such an embodiment of the invention is shown in FIG. 4 where six groups 21–26 of IR radiating elements are arranged across an area covered by a smoke 27. Each such group 21–26 consists of two IR radiating elements 28 and 29, where element 28 represents a background reference element, i.e. having the same radiation temperature as the background. Thus element 28 corresponds to element 0 in the previous embodiment. The radiation temperature of element 29 is selected in accordance with the scale 0–7 mentioned above, e.g. having a radiation temperature corresponding to the quality figure 4. The number of groups 21–26 with detectable temperature peaks then comprises a measure of the camouflaging capacity of the smoke over a large area.

In the embodiment of FIG. 2, the number of non-distinguishable radiation peaks is used as a measure of the quality of the smoke. Thus, the quality is given as a "quality figure". For instance, "quality figure 4" means that 4 radiation peaks cannot be distinguished. Similarly, "quality figure 7" means that none of the 7 radiators can be distinguished. Thus, the "quality figure 7" is the highest possible quality.

Thus, in the embodiment of FIG. 4 if all the radiators 29, which are distributed over a wide area, have the "quality figure 4", the embodiment enables one to detect in which parts of said wide area the smoke has the "quality figure 4". In certain cases, where one demands an extremely high degree of camouflage over said wide area, one can use radiators having the "quality figure 5", or perhaps "quality figure 6". However, in the embodiment shown in FIG. 4, we have chosen the radiator having the "quality figure 4", i.e., the radiator which has about the average radiation capacity.

The radiating elements in FIG. 4 are paired because the several radiating elements 29 should preferably each be accompanied by a reference element 28, which has the same function as the element "0" in FIG. 2, namely, to represent a background reference element, i.e., having the same radiation temperature as the background. The background reference elements "0" (FIG. 2) and element 28 (FIG. 4) can be deleted only if the proper radiation values for the other elements are set in another way with respect to the background radiation level. However, it has been found that the easiest way to set the correct radiation values of the several radiation elements 1 to 7 in FIG. 2 and of the element 29 in FIG. 4 is to make a comparison with an accompanying reference element, such as reference element "0" (FIG. 2) and element 28 (FIG. 4).

Instead of a single element 29 it is possible aternatively for several selected elements of the type shown in FIG. 2 to form part of each group 21–26.

I claim:

1. Method for measuring the camouflaging capacity of a smoke, comprising the following steps:
   (a) locating a predetermined number n of radiating elements side by side to form a group, n being an integer $>1$;
   (b) selecting the radiation intensities of said radiating elements such that the intensities are mutually different and increases on a scale with respect to the background radiation level;
   (c) locating a radiation detector facing towards said group of radiating elements;
   (d) spacing said radiating elements within said group sufficiently apart from one another such that said radiation detector can detect said radiating elements as n separate and individual items having mutually different high radiation intensity peaks;
   (e) discharging said smoke in an area between said radiation detector and said group of radiating elements, said smoke thereby causing a change of said background radiation level; and
   (f) counting the number of said radiation peaks which cannot be distinguished by said radiation detector with respect to said changed background radiation level.

2. Method in accordance with claim 1, wherein said radiation elements have exponentially increasing radiation intensities and are sequentially located with respect to said background radiation level.

3. Method in accordance with claim 1, wherein one of the radiating elements is selected to have the same radiation intensity as the background radiation level.

4. Method in accordance with claim 1, wherein said radiating elements provide IR radiation, said radiation intensity and radiation intensity peaks constitute radiation temperature and temperature peaks, respectively, and said background radiation intensity is the background temperature.

5. Method for measuring the camouflaging capacity of a smoke over a wide area comprising the steps of:
   (a) locating a predetermined number n of radiating elements side by side to form a group, n being an integer $>1$;
   (b) selecting the radiation intensities of said radiating elements such that the intensities are mutually different and increase on a scale with respect to the background radiation level;
   (c) distributing a plurality of said groups over said wide area;
   (d) locating a radiation detector facing towards said plurality of groups of radiating elements;
   (e) spacing said radiating elements within said group sufficiently apart from one another such that said radiation detector can detect said radiating elements as n separate and individual items having mutually different high radiation intensity peaks;
   (f) discharging said smoke in said wide area between said radiation detector and said plurality of groups of radiating elements, said smoke thereby causing a change of said background radiation level; and
   (g) counting the number of said radiation peaks from said groups which cannot be distinguished by said radiation detector with respect to said changed background radiation level.

* * * * *